United States Patent [19]

Rottmaier et al.

[11] 4,156,074

[45] May 22, 1979

[54] PROCESS FOR THE PREPARATION OF (THIO)HYDANTOINS MODIFIED BY AMIDE GROUPS

[75] Inventors: Ludwig Rottmaier; Rudolf Merten, both of Leverkusen, Fed. Rep. of Germany

[73] Assignee: Bayer Aktiengesellschaft, Leverkusen, Fed. Rep. of Germany

[21] Appl. No.: 897,677

[22] Filed: Apr. 19, 1978

[30] Foreign Application Priority Data

Apr. 22, 1977 [DE] Fed. Rep. of Germany ....... 2718102

[51] Int. Cl.$^2$ ............................................. C08L 75/02

[52] U.S. Cl. .................................... 528/322; 528/363; 548/310; 548/313

[58] Field of Search ............... 528/322, 363; 548/310, 548/313

[56] References Cited

U.S. PATENT DOCUMENTS

| | | | |
|---|---|---|---|
| 3,549,599 | 12/1970 | Merten | 528/68 |
| 4,089,860 | 5/1978 | Merten et al. | 548/310 |

*Primary Examiner*—Maurice J. Welsh
*Attorney, Agent, or Firm*—Connolly and Hutz

[57] ABSTRACT

Processes for the production of hydantoins substituted by amide groups wherein maleic acid imides or maleic acid monoamides are reacted with ureas.

12 Claims, No Drawings

PROCESS FOR THE PREPARATION OF (THIO)HYDANTOINS MODIFIED BY AMIDE GROUPS

The preparation of hydantoins modified by amide groups is known. In the process in question, these compounds are prepared by reacting aspartic acid esters with isocyanates or isothiocyanates, cyclising the thus-obtained reaction products to give hydantoin-5-acetic acid esters and reacting the resulting esters with amines to the amide under the elimination of alcohol.

It has now been found that hydantoins substituted by amide groups, preferably in the 5-position, may be obtained easily and in very good yields in a single-stage reaction by reacting ureas with optionally substituted maleic acid imides and/or maleic acid amide optionally prepared in situ.

Accordingly, the present invention relates to a process for the preparation of (thio)hydantoins substituted by amide groups, wherein maleic acid imides corresponding to the following general formula (I) and/or maleic acid amides corresponding to the following general formula (II):

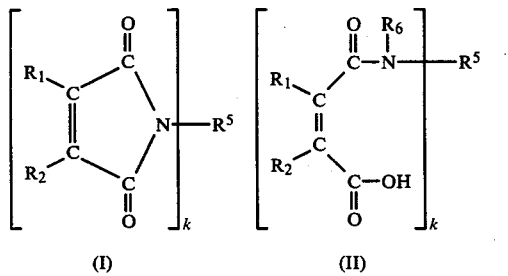

(I)      (II)

wherein $R_1$, $R_2$ and $R_6$, which may be the same or different, each represents hydrogen or an aliphatic radical;

$R_5$ represents hydrogen or an optionally substituted aliphatic, cycloaliphatic, aromatic, aliphatic-aromatic or heterocyclic radical; and k represents an integer of from 1 to 3, preferably 1 or 2;

are reacted with ureas.

Preferably $R_1$, $R_2$ and $R_6$ each represents hydrogen or a $C_1$–$C_{18}$ alkyl radical which may optionally be substituted by halogen preferably (chlorine or bromine); and $R_5$ represents hydrogen, a $C_1$–$C_{20}$ alkyl radical, a $C_5$–$C_{12}$ cycloalkyl radical which may optionally be substituted by halogen (preferably chlorine or bromine), by a hydroxy, $C_1$–$C_{18}$ alkoxy, $C_2$–$C_{18}$ alkoxy carbonyl or by a hydroxy carbonyl group, a $C_6$–$C_{16}$ aryl radical which may optionally be substituted by halogen (preferably chlorine or bromine), nitro, by $C_1$–$C_{18}$ alkyl, by $C_1$–$C_{18}$ halo alkyl, hydroxy, $C_1$–$C_{18}$ hydroxyalkoxy, $C_2$–$C_{18}$ alkoxy carbonyl or by hydroxy carbonyl groups, a $C_7$–$C_{18}$ aralkyl radical or a $C_5$–$C_{12}$ heterocyclic radical containing N, O and/or S atoms in the ring. Heterocyclic radicals are preferably aromatic or cycloaliphatic 5- or 6- membered rings which contain one or more oxygen, nitrogen and/or sulphur atoms, for example radicals derived from furan, pyridine, thiophene, imidazole, pyrimidine and piperazine. Particularly preferred meanings for $R_5$ are hydrogen, a $C_1$–$C_8$ alkyl radical, a $C_6$–$C_{16}$ aryl radical, such as phenyl, naphthyl, bis-phenyl or diphenyl radicals attached through O, S, $SO_2$, $CH_2$ $CH_3$—C—$CH_3$ or CO.

The term "(thio)hydantoins" as used herein including the claims means either or both hydantoins and thiohydantoins. Similarly, the term "(thio)ureas" as used herein including the claims means either or both ureas including polyureas and thioureas including polythioureas.

Particularly preferred acid mono amides corresponding to general formula (II) are acid mono amide of maleic acid, such as maleic acid amide, N-methylmaleic acid, N-butyl maleic acid, N-phenyl maleic acid monoamide, bis-maleic acid monoamides based on hexamethylene diamine, diaminodiphenyl methane, phenylene diamine, tolylene diamine and naphthylene diamine. Such maleic acid amides are produced by reacting maleic acid anhydride with the corresponding monoamines or polyamines.

The corresponding preferred maleic acid imides corresponding to general formula (I) are obtained from the above-mentioned maleic acid amides by the elimination of water.

The mono-or poly-ureas or thio ureas used in the reaction according to the present invention are preferably those corresponding to the following general formula III:

$$\left[ R^3-NH-C(=X)-NH-R^4 \right]_m \quad (III)$$

wherein $R_3$ and $R_4$, which may be the same or different, have the same meaning as $R_5$;

X represents oxygen or sulphur; and m represents an integer of from 1 to 100, preferably from 1 to 3 and, with particular preference, 1 or 2.

With particular preference, $R^3$ and $R^4$, which may be the same or different, represent a $C_1$–$C_{18}$ alkyl radical, a $C_5$ or $C_6$ cycloalkyl radical or a $C_6$–$C_{16}$ aryl radical optionally substituted by halogen, by $C_1$–$C_3$ alkyl or by $C_1$–$C_3$ alkoxy groups, such as phenyl, naphthyl, bisphenyl, benzyl or diphenyl radicals attached through O, S, $SO_2$, —$CH_2$—, $CH_3$—C—$CH_3$ or CO. It is preferred above all to use ureas for the process according to the present invention such as urea, methyl urea, butyl urea, N,N'-dimethyl urea, N,N'-diethyl urea, N,N'-dibutyl urea, N,N'-dicyclohexyl urea, N-methyl-N'-phenyl urea, N-methyl-N'-chlorophenyl urea, N-methyl-N'-dichlorophenyl urea, N-cyclohexyl-N'-chlorophenyl urea, phenyl urea, N,N'-diphenyl urea, bis-ureas of 4,4'-diisocyanato diphenyl methane or the technical isomer mixtures thereof and cyclohexyl amine or aniline, of 2,4- and 2,6-tolylene diisocyanate or technical mixtures thereof and cyclohexyl amine or aniline, of p- or m-phenylene diisocyanate and cyclohexyl amine or aniline, of hexamethylene diisocyanate and aniline, of isophorone diisocyanate and aniline, polyureas of the above-mentioned diisocyanates and hexamethylene diamine, isophorone diamine, 2,4- and 2,6-tolylene diamine and technical mixtures thereof, p or m-phenylene diamine, 4,4-diaminodiphenyl methane or the technical isomer mixture thereof.

The process according to the present invention may be illustrated by the following equations:

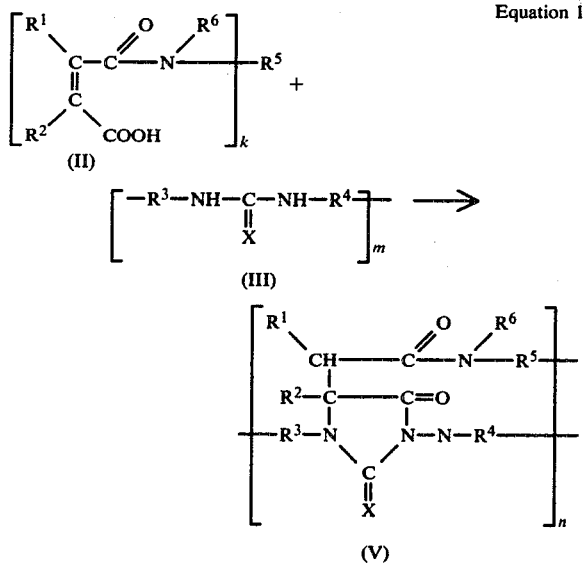

Equation 1

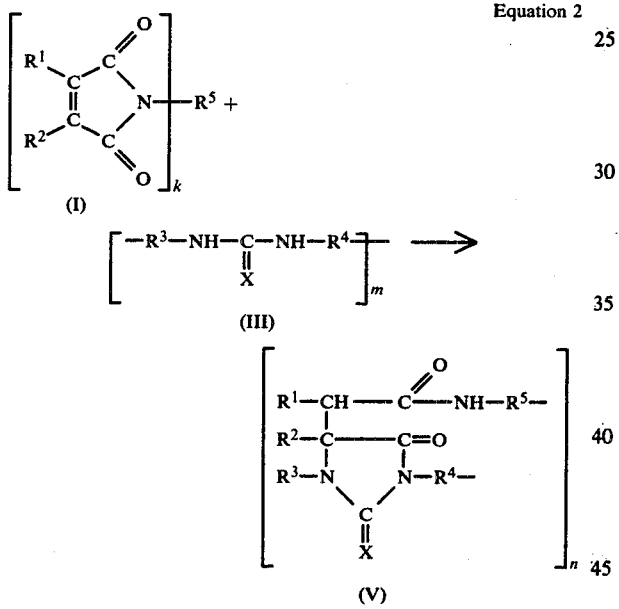

Equation 2 wherein

R$_1$–R$_6$ are as defined above and, when k and m=1, a monomolecular compound is formed and, when k and/or m>1, a high molecular compound is formed, the hydantoin rings being attached through the radicals R$_5$ and/or R$^3$ and/or R$^4$; and n represents an integer of from 1 to 1000, preferably from 1 to 100.

The reaction between the maleic acid amides and the ureas and between maleic acid imides and the ureas is generally carried out at temperatures of from 80° to 250° C., preferably from 150° to 200° C., optionally in inert solvents.

Preferred inert solvents are aliphatic or aromatic hydrocarbons and the halogenation products thereof, such as diisopropyl benzene, methyl naphthalene, di- or tri-chlorobenzene, or polar solvents, such as N-methyl pyrrolidone, dimethyl formamide, dimethyl acetamide, phenol, cresols or xylenols.

In general, reaction times of from 1 to 10 hours are necessary. The addition and cyclisation reactions gener- ally can be carried out under the effect of heat. In order to facilitate the reaction, it is advantageous in many cases to add a catalyst, particularly acid reagents. In cases where acid solvents, for example phenols and cresols, are used, the acidity thereof is sufficient for carrying out the reaction in sufficiently short reaction times. In other cases, acetic acid, butyric acid, pivalic acid or benzoic acid, for example, may be added. In addition, this reaction is accelerated by basic catalysts, such as triethyl amine, dimethyl aniline or Dabco ® (1,4-diazabicyclo-[2,2,2]-octane).

The reaction is generally carried out using stoichio- metric quantities. However, it is also possible to use one of the components in excess in order to obtain polymers containing further reactive groups. The reaction prod- ucts are worked up in the conventional way, for exam- ple by distillation or crystallisation processes. Poly- meric products may be directly stoved onto metal sheets or wires in known manner. However, they may also be obtained in pure form by precipitation, for exam- ple with acetone or methanol, and thus processed into films for example.

The hydantoins modified by amide groups which are obtained in accordance with the present invention may be incorporated into a variety of different polymers through an amide group and, optionally, in the presence of further by reaction with mono-or poly basic carbox- ylic acids and derivatives by reaction with mono-or poly-carboxylic acids and derivatives thereof or with monohydric alcohols or polyhydric alcohols to form polyesters having increased thermal stability.

The monohydantoins may be used in the plant protec- tion or pharmaceutical fields.

The polyhydantoins according to the present inven- tion are distinguished by the particular temperature resistance thereof and are suitable for use as adhesives, lacquers, films and mouldings. The properties thereof may be varied within wide limits for the various appli- cations by the addition of fillers, pigments and low and high molecular weight components, for example for the production of lacquers and films by mixing with polyes- ters or poly amides.

EXAMPLE 1

1,3-dimethyl-5-(phenylaminocarbonyl-methylene)- hydantoin

A solution of 17.3 parts of N-phenyl maleic imide and 8.8 parts of N,N'-dimethyl urea in 100 parts of cresol is stirred for three hours at 190° C. The solvent is distilled off in vacuo and the residue fractionated. The oily liq- uid which distills at a boiling point of 220° C./0.1 Torr solidifies after a while and may be recrystallised from n-propanol (Mp. 114°–115° C.). IR and NMR-spectra confirm the assumed compound.

Analysis: calculated: C=59.8%; H=5.75%; N=16.05%. Observed: C=59.8%; H=5.8%; N=16.1%.

EXAMPLE 2

3-phenyl-5-(phenyl aminocarbonyl-methylene)- hydantoin 17.3 parts of N-phenyl maleic imide and 13.6 parts of phenyl urea are dissolved in 100 parts of cresol and the resulting solution is stirred for 6 hours at 200° C. The solvent is distilled off and the residue dissolved, with heating, in 100 parts of ethanol. The deposit which accumulates on cooling is filtered off under suction, washed and dried and, for complete purification, may be recrystallised from glycol monomethylether acetate (Mp. 234°-235° C.). IR- and NMR- spectra confirm the assumed structure.

Analysis: calculated: C=66.0%; H=4.85%; N=13.6%. Observed: C=66.2%; H=4.93%; N=13.4%.

EXAMPLE 3

1-methyl-3-(2-chloro)-phenyl-5-(2-chlorophenyl aminocarbonyl-methylene)-hydantoin 36 parts of N-(2-chloro)-phenyl maleic imide, 100 parts of cresol and 32.1 parts of N-methyl-N'-(2-chloro)-phenyl urea are stirred for two hours at 200° C. and concentrated in vacuo. The oily residue is dissolved, with heating, in 100 parts of ethanol. 57.7 parts of the required compound crystallise out on cooling and may be additionally purified by recrystallisation from a mixture of ethanol and ethyl acetate (Mp. 172°-173° C.). IR- and NMR-spectra confirm the assumed compound.

Analysis: calculated: C=55.2%; H=3.83%; N=10.72%; Cl=18.1%. Observed: C=55.1%; H=3.8%; N=10.6%; Cl=18.0%.

EXAMPLE 4

1-methyl-3-(3,4-dichloro)-phenyl-5-(3,4-dichlorophenylaminocarbonyl methylene)-hydantoin A mixture of 79 parts of N-(3,4-dichloro)-phenyl maleic imide, 72.5 parts of N-methyl-N-(3,4-dichloro)-phenyl urea and 200 parts of cresol is stirred for four hours at 200° C. and concentrated in vacuo. The viscous residue is boiled with 250 parts of ethanol and the deposit (85 parts) obtained after cooling is filtered off under suction, washed and dried. For complete purification, the substance obtained is recrystallised from glycol monomethylether acetate (Mp. 183°-184° C.). IR- and NMR-spectra confirm and assumed structure.

Analysis: calculated: C=46.9%; H=2.82%; N=9.12%; Cl=30.8%. Observed: C=46.6%; H=3.0%; N=8.8%; Cl=30.5%.

EXAMPLE 5

A suspension consisting of 35.8 parts of N,N'-bis-maleic imide-4,4'-diphenyl methane, 190 parts of cresol, 0.1 part of Dabco ® and 44.8 parts of the bis-urea of 1 mole of 4,4'-diisocyanatodiphenyl methane and 2 moles of cyclohexyl amine are slowly heated to 200° C. The solution formed is stirred for ten hours at 200° C. 269 parts of a 30% amide modified polyhydantoin solution are obtained. After dilution to 15%, this solution has a viscosity at 25° C. of 506 cP. According to the IR-spectrum (bands characteristic of hydantoin at 1715 and 1770 cm$^{-1}$ and of amide at 1690 cm$^{-1}$), the product is a polymer containing the following recurring structural unit. A lacquer film stoved onto a sheet of metal shows very good thermal properties coupled with high elasticity.

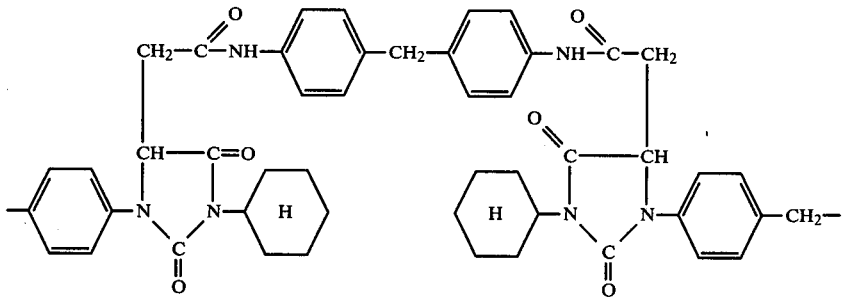

EXAMPLE 6

1,3-dimethyl-5-(phenylaminocarbonyl methylene)-hydantoin

A mixture of 19.1 parts of N-phenyl maleic acid monoamide 8.8 parts of N,N'-dimethyl urea and 100 parts of cresol is stirred for 2.5 hours at 165° C. The solvent is distilled off in vacuo and the residue fractionated. An oily liquid distills over at a boiling point of from 220° to 223° C./0.1 Torr and solidifies after a while. Recrystallisation from n-propanol gives the compound confirmed by IR- (bands characteristic of hydantoins at 1705 and 1765 cm$^{-1}$ and of amide at 1690 cm$^{-1}$) and NMR-spectra.

Analysis: calculated: C=59.8%; H=5.75%; N=16.05%. Observed: C=59.7%; H=5.7%; N=16.1%.

EXAMPLE 7

1-cyclohexyl-3-phenyl-5-(phenyl aminocarbonyl methylene)-hydantoin 95.5 parts of N-phenyl maleic amide acid and 108.5 parts of N-cyclohexyl-N'-phenyl urea are dissolved, with heating, in 200 parts of cresol and the resulting solution stirred for 2.5 hours at 170° C. The solvent is distilled off and the hot residue is dissolved in 200 parts of ethanol. 100 parts of the assumed, almost pure compound melting at 197° C. crystallise out on cooling. The compound is confirmed by IR-(bands characteristic of hydantoin at 1710 and 1770 cm$^{-1}$ and of amide at 1695 cm$^{-1}$) and NMR-spectra.

Analysis: calculated: C=70.6%; H=6.4%; N=10.7%. Observed: C=70.5%; H=6.5%; N=10.6%.

EXAMPLE 8

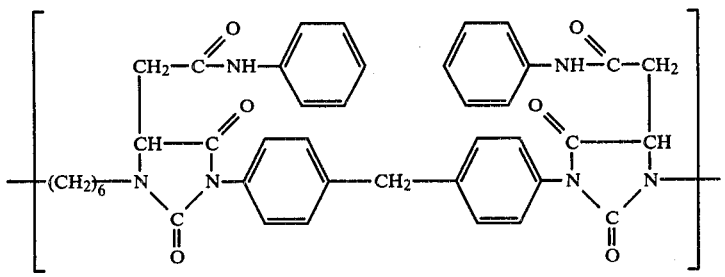

A suspension consisting of 191 parts of N-phenyl maleic acid amide and 183 parts of a polyurea produced from 1 mole of hexamethylene diamine and 1 mole of 4,4′-diisocyanatodiphenylmethane in 831 parts of cresol is heated to 180° C. following the addition of 0.1 part of triethylene diamine and stirred for 7 hours at 180° C. 1190 parts of a 30% amide-modified polyhydantoin solution are obtained. After dilution to 15% this solution has a viscosity of 116 $cp_{25}$. According to the IR-spectrum (bands characteristic of hydantoin at 1715 and 1770 $cm^{-1}$ and of amide at 1690 $cm^{-1}$), the product obtained is a polymer containing the recurring structural unit shown above. A lacquer film stoved onto a sheet of metal shows very good thermal properties coupled with high elasticity.

We claim:

1. Processes for the production of (thio) hydantoins substituted by amide groups, wherein maleic acid imides corresponding to formula (I) and/or maleic acid mono amide corresponding to formula (II):

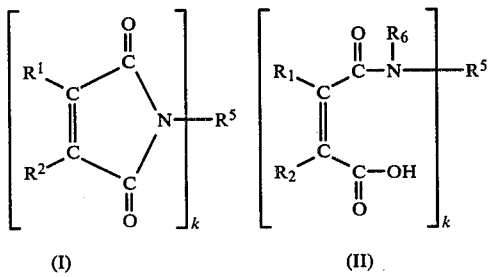

wherein $R_1$, $R_2$ and $R_6$, which may be the same or different, each represents, hydrogen or an aliphatic radical;

$R_5$ represents hydrogen or an optionally substituted aliphatic, cycloaliphatic, aromatic, aliphatic-aromatic or heterocyclic radical; and k represents an integer of from 1 to 3 are reacted with (thio) ureas.

2. Processes as claimed in claim 1 wherein $R_1$, $R_2$ and $R_3$ each represents hydrogen or a $C_1$–$C_{18}$ alkyl radical which may optionally be substituted by halogen, $R_5$ represents hydrogen, a $C_1$–$C_{20}$ alkyl radical, a $C_5$–$C_{12}$ cycloalkyl radical which may optionally be substituted by halogen, by a hydroxy, $C_1$–$C_{18}$ alkoxy, $C_2$–$C_{18}$ alkoxy carbonyl or by a hydroxy carbonyl group, a $C_6$–$C_{16}$ aryl radical which may optionally be substituted by halogen, nitro, by $C_1$–$C_{18}$ alkyl, by $C_1$–$C_{18}$ haloalkyl, hydroxy, $C_1$–$C_{18}$ hydroxylalkoxy, $C_2$–$C_{18}$ alkoxy carbonyl or by hydroxy carbonyl groups, a $C_7$–$C_{18}$ aralkyl radical or a $C_5$–$C_{12}$ heterocyclic radical containing N, O and/or S atoms in the ring.

3. Processes as claimed in claim 2, wherein $R_5$ represents hydrogen, an optionally substituted $C_1$–$C_8$ alkyl radical or $C_6$–$C_{16}$ aryl radical.

4. Processes as claimed in claim 1, wherein the (thio) urea corresponds to formula (III)

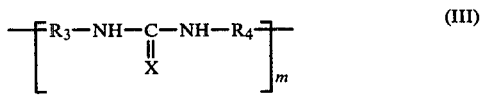

wherein $R_3$ and $R_4$, which may be the same or different, each represents hydrogen or an optionally substituted aliphatic, cycloaliphatic, aromatic, aliphatic-aromatic or heterocyclic radical;

X represents oxygen or sulphur; and m represents an integer of from 1 to 100.

5. Processes as claimed in claim 4, wherein $R_3$ and $R_4$, have the same meaning as $R_5$.

6. Processes as claimed in claim 4, wherein $R_3$ and $R_4$ represent hydrogen, a $C_1$–$C_{18}$ alkyl radical, a $C_5$ or $C_6$ cycloalkyl radical or a $C_6$–$C_{16}$ aryl radical optionally substituted by halogen, by $C_1$–$C_3$ alkyl or by $C_1$–$C_3$ alkoxy groups, and m an integer from 1 to 3.

7. Processes as claimed in claim 6, wherein, m represents 1 or 2.

8. Processes as claimed in claim 1, carried out at a temperature of from 80° to 250° C.

9. Processes as claimed in claim 8, wherein the said temperature is from 150° to 200° C.

10. Processes as claimed in claim 1, carried out in an inert solvent.

11. An amide substituted (thio)hydantoin produced by the process as claimed in claim 1.

12. A lacquer composition comprising an amide-substituted (thio)hydantoin as claimed in claim 11.

* * * * *